United States Patent
Maughan et al.

(10) Patent No.: US 10,413,171 B2
(45) Date of Patent: Sep. 17, 2019

(54) OPHTHALMIC METHOD AND APPARATUS FOR NONINVASIVE DIAGNOSIS AND QUANTITATIVE ASSESSMENT OF CATARACT DEVELOPMENT

(71) Applicants: David Maughan, Burlington, VT (US); Alexander Kochis, Seattle, WA (US); Guy Kennedy, Underhill, VT (US)

(72) Inventors: David Maughan, Burlington, VT (US); Alexander Kochis, Seattle, WA (US); Guy Kennedy, Underhill, VT (US)

( * ) Notice: Subject to any disclaimer, the term of this patent is extended or adjusted under 35 U.S.C. 154(b) by 0 days.

(21) Appl. No.: 16/197,841

(22) Filed: Nov. 21, 2018

(65) Prior Publication Data

US 2019/0183329 A1 Jun. 20, 2019

Related U.S. Application Data

(63) Continuation-in-part of application No. 15/652,274, filed on Jul. 18, 2017, now Pat. No. 10,165,943.

(51) Int. Cl.
| | |
|---|---|
| *A61B 3/02* | (2006.01) |
| *A61B 3/024* | (2006.01) |
| *A61B 3/18* | (2006.01) |
| *A61B 3/06* | (2006.01) |
| *A61B 3/00* | (2006.01) |

(52) U.S. Cl.
CPC ............ *A61B 3/024* (2013.01); *A61B 3/0041* (2013.01); *A61B 3/066* (2013.01); *A61B 3/18* (2013.01)

(58) Field of Classification Search
CPC ......... A61B 3/024; A61B 3/0041; A61B 3/18; A61B 3/066; A61B 3/103; A61B 3/1208; A61B 3/152
USPC ........................................................ 351/211
See application file for complete search history.

(56) References Cited

U.S. PATENT DOCUMENTS

| | | | | |
|---|---|---|---|---|
| 2012/0164613 A1* | 6/2012 | Jung | ...................... | G06Q 30/02 434/236 |
| 2016/0353987 A1* | 12/2016 | Carrafa | .................. | A61B 3/032 |
| 2017/0042416 A1* | 2/2017 | Carrafa | ................ | A61B 3/0041 |

* cited by examiner

*Primary Examiner* — William R Alexander
*Assistant Examiner* — Henry A Duong

(57) ABSTRACT

An ophthalmic method and apparatus for noninvasive diagnosis and quantitative assessment of cataract development and/or color blindness is provided. The method and apparatus with direct feedback from the subject, or historical data, provides a quantitative method for noninvasive diagnosis and quantitative assessment of cataract development. Also included is a mobile apparatus comprising a set of executable instructions that configures the mobile apparatus to determine an opacity of a cataract lens.

11 Claims, 3 Drawing Sheets

OPHTHALMIC METHOD AND APPARATUS FOR NONINVASIVE DIAGNOSIS AND QUANTITATIVE ASSESSMENT OF CATARACT DEVELOPMENT

CROSS-REFERENCE TO RELATED APPLICATIONS

The present application is related to, claims the earliest available effective filing date(s) from (e.g., claims earliest available priority dates for other than provisional patent applications; claims benefits under 35 USC § 119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith:

U.S. patent application Ser. No. 15/652,274, entitled "OPHTHALMIC METHOD AND APPARATUS FOR NONINVASIVE DIAGNOSIS AND QUANTITATIVE ASSESSMENT OF CATARACT DEVELOPMENT", naming David W. Maughan as first inventor, filed 18 Jul. 2017.

BACKGROUND

1. Field of Use

The present invention generally relates to noninvasive determination of disease states. More particularly, the present invention relates to a method and apparatus for noninvasively determining an ocular disease state, and for noninvasively determining the rate of development of this ocular disease state.

2. Description of Prior Art (Background)

The healthy human eye contains a clear lens that focuses light rays onto the retina. Clouding of the lens is called a cataract. A cataract causes decreased vision by interfering with the normal transmission, of light through the eye's clear lens onto the retina. The degree of visual loss is determined by cloudiness of the lens and the location in the lens where the cloudiness occurs. Cataracts are uncommon in children and young adults: however nearly everyone develops cataracts as they age due to cumulative oxidative damage (stress) to the lens. Approximately 70% of people develop cataracts by 75 years of age according to the American Academy of Ophthalmology.

Lens abnormalities include: senile nuclear cataract (the most common age-related cataract), senile cortical cataract (also an age-related cataract), congenital cataract, embryonic nuclear cataract, anterior polar cataract, lenticonus cerulean opacities, sub capsular cataract, posterior subcapsular cataract, cortical cataract, mature cataract, shield cataract, traumatic cataract, bilateral lens distortion, lenticulocorneal adhesion, Christmas tree cataract (indicative of myotonic dystrophy) and sunflower cataract (indicative of Wilson disease).

A person with a mature cataract, which significantly impairs, visual function, may be treated by surgically extracting the impaired lens of the person and replacing it with either an intraocular lens or an extraocular lens. However, the condition cannot be addressed until the cataract is properly diagnosed or determined.

Many different methods and apparatus are known in the prior art to help determine the existence or extent of a cataract. These methods and apparatus generally make the determination based either on visual acuity tests or on an analysis of light exiting the eye of the patient. However, due to various anomalies these prior art approaches may not be optimum indicators of a cataract. In the case of visual acuity tests which depend upon light reaching the retina, the use of high contrast letters or figures may enable the patient to recognize the letters and figures and thus "pass" the visual acuity test regardless of a cataract condition.

Similarly, another test compares a photograph of a person's lens to a standardized series of photographs showing lenses with different degrees of cataract formation in different parts of the lens. However, the photographic images depend upon back scattered light from the lens. Because the back scattered light may not correlate highly with the location of the cataract and what the patient sees, a clinician using the photographs as the basis of an analysis will not be able to accurately determine the effect of opacities upon the patient's visual function and accordingly the patient may "pass" or may "fail" the test incorrectly. In U.S. Pat. No. 4,863,261, issued to J. Flammer, entitled "Method of and Apparatus for Measuring the Extent of Clouding of the Lens of a Human Eye," light exiting the eye, i.e. "back scattered" light, is analyzed with respect to incident radiation to determine the extent of clouding of the lens.

Cataract detection using scattering techniques is also described in Benedek et al., in U.S. Pat. No. 4,993,827 for "Method for Detecting Cataractogenesis", issued Feb. 19, 1991. Benedek et al. collects and determines the intensity of light scattered from a measurement location in the lens and compares this value to the intensity of light scattered by a normal clear lens to determine the degree of cataractogenesis at the specific measurement location.

Another scattering detection technique is described in Taratuta et al., in U.S. Pat. No. 5,072,731 for "Apparatus for Detecting Cataractogenesis Using Quasielastic Light Scattering", issued Dec. 17, 1991. Taratuta et al. analyzes the light scattered from the lens using an autocorrelation function, or the power spectrum, to separate the light fluctuation into two components: one caused by fast diffusing proteins and one caused by slow diffusing protein aggregates. The data is then compared to reference curves to determine the degree of cataractogenesis.

In each of the above back scattering techniques, low intensity light must be incident upon the eye in order to avoid damage to the eye. Because of the limited incident intensity, only a small amount of light is reflected back to a photomultiplier of limited quantum efficiency for measurement. The limited amount of reflected light and limited quantum efficiency of the photomultiplier make accurate analysis difficult.

Kandel et al. in U.S. Pat. No. 5,908,394 describes a complicated method of quantifying cataract disease states in the human lens, which builds on a centuries-old observation that colors are perceived differently due to differential light absorption in the lens; in particular, light toward the blue and violet wavelength of the spectrum is absorbed by a cataract more than light toward the green and red wavelengths of the spectrum. This phenomenon is responsible for various degrees of color "blindness" that have long been observed by people with, cataracts.

In Kandel et al. the subject is asked to determine when 1) two non-monochromatic light spots are identical in "color, hue, and saturation" as the mix of colors is varied, with 2) intensity remaining equal. That is, color mix is varied, but light intensity is not. The preferred embodiment for the light source specified is a Tungsten Halogen bulb that provides, white light to various color filters (with fairly broad bands); attenuation of light is achieved by a neutral density "electro-optic polarizer followed by a variable pi-cell".

Kontadakis et al., J. Cataract Refract. Surg. 2011: Kontadakis et al. evaluated human lens opacity using heterochromatic flicker photometry (HFP), a standard method for assessing macular pigment optical density. Kontakakis et al. employed a commercial instrument (MPS 9000 QuantiEye Macular Pigment Screener, Tinsley Ophthalmic Instruments, Inc.) equipped with light emitting diodes (LED) of 465 nm (blue) and 530 nm (green) wavelengths, that flickered in counter-phase on a white-light pedestal. Opacity (ocular media density), determined from the comparative attenuation of the blue test light versus the green reference light, was assessed by instructing the subject to minimize or eliminate the perception of flicker, by adjusting the intensity of the blue test light while keeping the intensity of the green reference light constant.

As with the Kandel's invention, the Kontaclakis et al. application is an adaptation of a well-known observation that the absorption properties of tinted intraocular lenses resemble that of aging human lenses; while un-tinted intraocular lenses resemble the lower levels of blue light attenuation found in younger lenses.

Teikari et al., J. Opt. Soc. Am. A. 2012: Teikari et al. describes a further refinement of the use of heterochromatic flicker photometry (HFP). Light attenuation in the human lens was approximated by fitting absorbance differences, measured using a custom-built HFP instrument with a mathematical model of ocular media age-dependency.

The commercial LEDs (LedEngin, Inc. & Philips, Inc.) in Teikari et al. have wavelength peaks at 405 nm and 530 nm and is based on the well-known phenomenon (of differential blue versus green light absorbance in the human lens).

Van Best et al., Invest. Opthalniol. Vis. Sci. 1985: Van Best et al. 1985 describes another method of determining the properties of blue-green light transmission through the human lens using standard techniques of autoflurophotometry. Lens transmission is calculated from peak autofluorescence values (comparing peak autofluorescence values in the anterior and posterior part of the lens) in diabetic patients and healthy controls. Autofluorescence is measured with computer flurorophotometer (Fluorotron Master of Coherent Radiation, Inc.). The light wavelengths are set by the instrument's color filters, which had fairly broad bands with peaks at 490 nm and 530 nm.

As seen the prior art solutions are often complicated and/or intricate methods and systems used to determine the presence of a cataract. These prior art solutions often require the presence of a physician or medical professional in a medical facility to administer the cataract test and interpret the results. Thus, a need exists for a mobile and improved, noninvasive, ocular disease state determination that does not require complicated medical facilities.

BRIEF SUMMARY

One embodiment of the present invention is an, ophthalmic optoelectronic method and apparatus that, with direct feedback from the subject, or historical data, provides a quantitative method for noninvasive diagnosis and quantitative assessment of cataract development. The method includes superimposing a symbol field (SF) over a background field (BF), wherein SF and BF comprise a plurality of pixelated dots or symbols, each having Red, Green, Blue (RGB) values. The method first determines the RGB values for SF to be discernable from BF with a cataract free lens and records the RGB values for the cataract free lens. RGB values for a cataract free lens may be determined in-situ, e.g., with a known cataract free lens, or, from historical data. Resetting the RGB values, the next method step views the SF and the BF simultaneously with a suspected cataract lens and adjusts the RGB values until SF is discernable from BF. The method records RGB values for the cataract lens and determines the opacity of the cataract lens from the recorded RGB values, creating an index OC.

The invention is also directed towards a mobile apparatus having a set of executable instructions that configures the mobile apparatus to determine an opacity of a cataract lens and/or color blindness. The executable instructions include superimposing a symbol field (SF) over a background field (BF), wherein SF and BF comprise a plurality of pixelated dots or symbols having Red, Green, Blue (RGB) values. The executable instructions include determining the cataract free RGB values for SF to be discernable from BF and recording the cataract free RGB values. The executable instructions include instructions for viewing the SF and the BF simultaneously with a cataract lens and adjusting the cataract lens RGB values until SF is discernable from BF; and recording cataract lens RGB values for the cataract lens. The executable instructions determine the opacity of the cataract lens from the recorded RGB values. The executable instructions also include instructions for determining color blindness.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION

The following brief definition of ten is shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example; and If the specification states a component or feature "may," "can," "could," "should," "preferably," "possibly," "typically," "optionally," "for example," or "might" (or other such language) be included or have a characteristic, that particular component or feature is not required to be included or to have the characteristic.

Figures 1A, 1B:
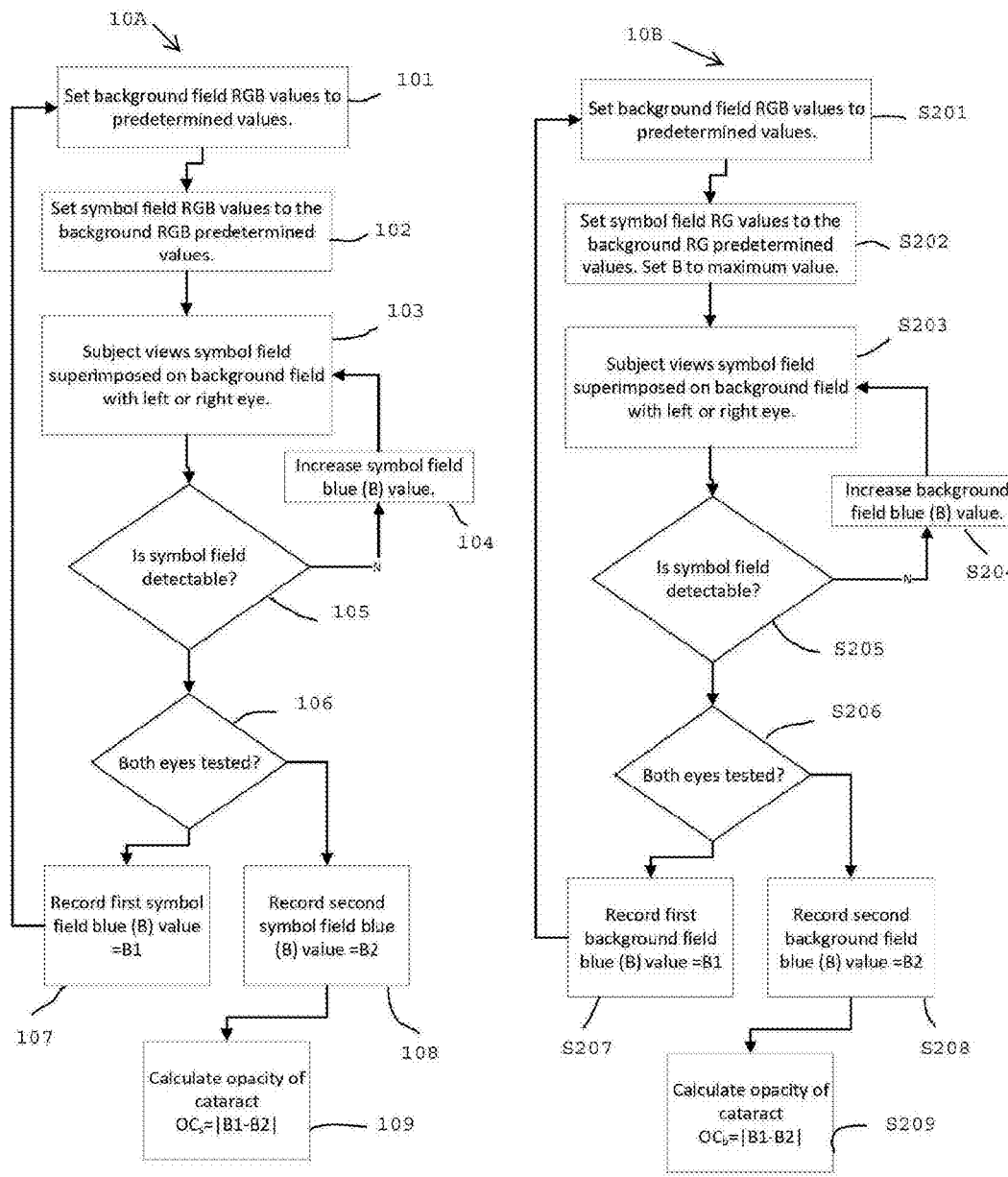
FIG. 1A is a flow chart for one method of detecting cataracts in accordance with the invention described herein.
FIG. 1B is a flow chart for an alternate method of detecting cataracts in accordance with the invention described herein.
Figure 2A:
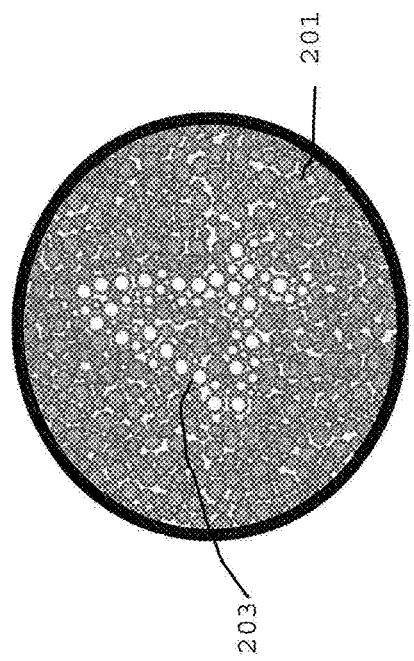
FIGS. 2A, 2B, 2C, and 2D are example subsets of a series of cataract detection plates in accordance with the invention in FIG. 1A.
Figure 2B:
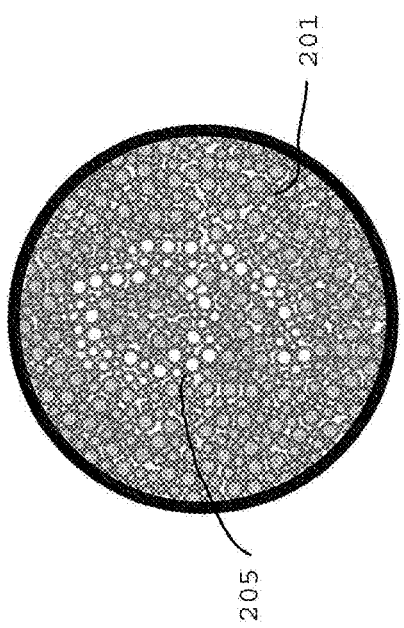
Figure 2C:
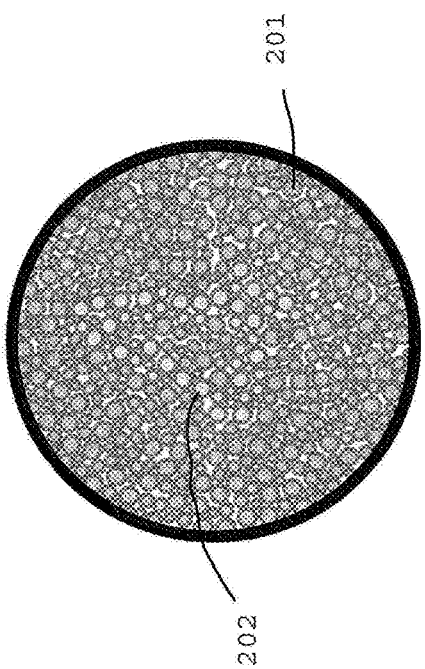
Figure 2D:
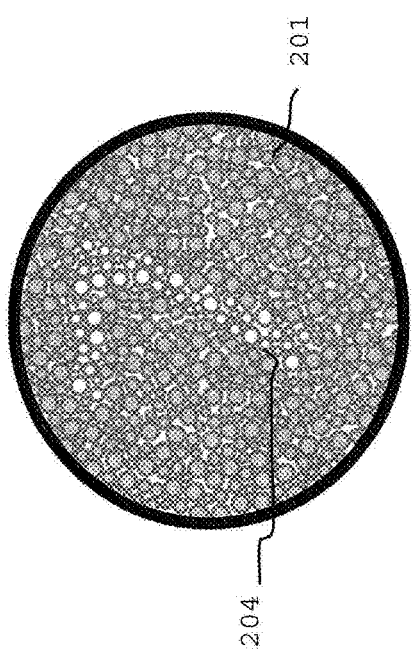

Referring to FIG. 1A and FIGS. 2A, 2B, 2C, and 2D there is shown a flow chart of one method 10A for implementing features of the present invention, and an example subset of a series of cataract detection plates in accordance with the invention in FIG. 1A, respectively.

An exemplar result is illustrated in FIG. 1A and FIGS. 2A, 2B, 2C, and 2D for a subject with a cataract intraocular lens (CIL) in the right eye and a native lens (no CIL) in the left eye. Background 201 Red, Green, Blue (RGB) values are set to a predetermined level 101 (R146, G208, B95). Symbol 202 RGB values are set to the background 201 RGB values. The subject then views 103 the symbol field 202 superimposed on the background field 201. If the symbol 202 is not visible the symbol 203 blue value B (B155) is increased 104. The subject views 103 the symbol field. 203 superimposed on the background field 201. If the symbol 203 is not visible the symbol 203 blue value B is increased 104. The subject views 103 the symbol field 204 superimposed on the background field 201. If the symbol 204 is not visible the symbol 204 blue value B (B215) is increased 104. The subject views 103 the symbol field 205 superimposed on the background field 201. If the symbol 205 is visible the symbol 205 blue value B1 (B215) is recorded 107. The procedure is repeated for the other eye such that two symbol Blue values are recorded, B1, B2, one for each eye. The cataract opacity $OC_s$ is calculated as the absolute difference between B1 and B2, where the subscript "s" implies that the symbol B value was varied and the background values were held constant.

It will be appreciated that the subject or user may have cataracts in both eyes at the time of the test. In that case the user may compare previously stored data (See FIG. 3) with the stored "cataract free" lens data. In addition, the user may also use historical norms for the user's age and gender as the "cataract free" lens data.

Still referring to FIGS. 2A, 2B, 2C, and 2D, for example, viewing the superimposed symbol image 202 through the right eye (CIL) and increasing the value of symbol blue (B) from 95 to 255 (the maximum value tested), where the value is given in arbitrary units, the subject perceives a blue-tinted symbol which, at a value of 155, became "just detectable" against the green-tinted background. Further increases in the value of blue (to 255) produced a "very sharp" image of the symbol against the background pattern.

In contrast, upon viewing the image 202 through the left eye (with the cataract) and also increasing the value of symbol blue in the same way as before, the symbol becomes "just detectable" at 215, a value significantly above that perceived by the right eye—indicating the presence of a cataract. Further increases in the value of symbol blue (to 255) again produces a "sharp" image (not quite as sharp as that of the right eye) of the symbol against the background pattern. Using the eye with the CIL as a "no cataract" reference, the difference between the blue values at the "just detectable" threshold (60=215−155) is a measure of opacity (or index) of the cataract. Subjects whose cataracts are not as developed as this example will generally have an index less than 60: subjects with more developed cataracts will have an index greater than 60. Subjects with no cataracts have an index of zero, by definition (as measured in an eye with a CIL or in an eye of a young subject with no discernable cataracts, as determined by an eye doctor).

In the examples shown FIGS. 2A, 2B, 2C, and 2D, the subject has a cataract intraocular lens (CIL) in the right eye and the native lens (no CIL) in the left eye. Viewing the image 202 through the right eye (CIL) and increasing the value of blue (B) from 95 to 255 (arbitrary units), a blue-tinted "4" 203 becomes "just detectable" at 155 against the background pattern of green-tinted dots 201. Further increases in the value of blue (to 255) produces a "very sharp" image of the symbol against the background pattern.

In contrast, upon viewing the image 202 through the left eye (with the cataract) and increasing the value of blue from 95 to 255, a "7" becomes "just detectable" at 215, i.e., a value significantly above that of the right eye, thereby indicating the presence of a cataract. Again, a further increase in the value of blue (to 255) produced a "sharp" image of the symbol against the background pattern.

Using the eye with the CIL as a "no cataract" reference, the difference between the blue values at the "just detectable" threshold (71=215−141) is a measure of opacity (or index) of the cataract. A background pattern value 201 for blue was maintained at 80 throughout, with values of red and green maintained at 146 and 208 for both symbol and background patterns.

An alternate embodiment is illustrated in FIG. 1B. Background Red, Green, Blue (RGB) values are set to a predetermined level S201, Symbol RG values are set to the background S201 RG values, while symbol B value is set to a maximum value S202. The subject then views S203 the symbol field superimposed on the background field. If the symbol is not visible the symbol blue value B is increased S204. The subject views S203 the symbol field superimposed on the background field. If the symbol is not visible the background blue value B is increased S204. The procedure is reiterated until the symbol is visible. The procedure is repeated for the other eye such that two symbol Blue values are recorded, B1, B2 one for each eye. The cataract opacity $OC_s$ is calculated as the absolute difference between B1 and B2, where the subscript "b" implies that the background B value was varied and the symbol values were held constant.

Figure 3:
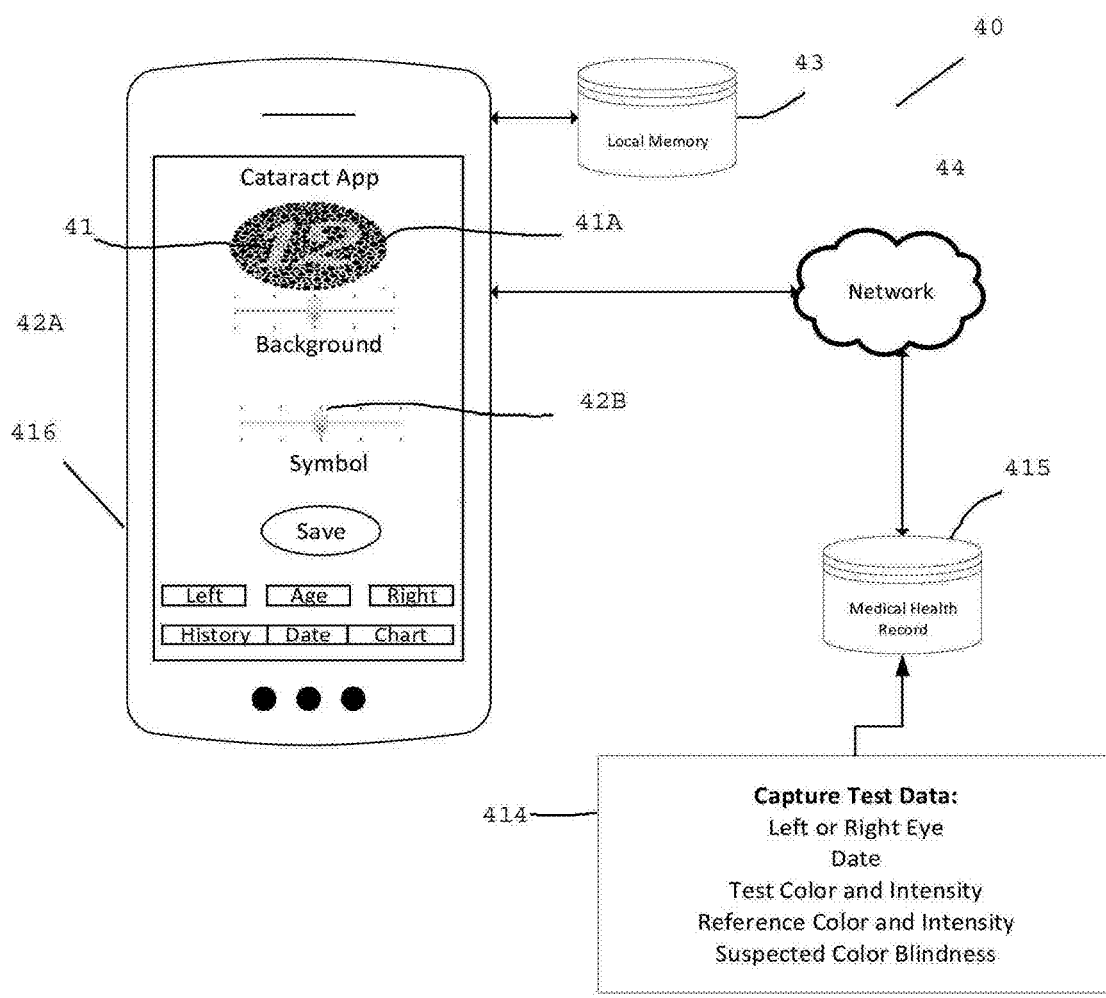
FIG. 3 is a system flow chart for one method of detecting cataracts and color blindness in a mobile device in accordance with the invention shown in FIG. 1A or FIG. 1B.

Referring also to FIG. 3 there is shown a system flow chart for one method and system 40 of detecting cataracts or color blindness in a mobile device in accordance with the method shown in FIG. 1A or FIG. 1B. Device 416 may be any suitable device such as a tablet, cell phone, or other mobile device. It will be appreciated that the device 416 includes resources, e.g., microprocessors, memory and logic circuits, for implementing the invention described herein.

The user adjusts either the test symbol 41 blue value, or the background blue value 41A as described in FIG. 1A or FIG. 1B, respectively with adjusters 42A or 42B. It will be understood that that adjusters 42A or 42B may be adapted to adjust each of the RGB values for the test symbol 41 or background 41A.

It will also be appreciated that the system may select colored images, presented in sequence, which are based on Ishihara images (namely, a circle of dots appearing randomized in color and size). Within the pattern are dots which form a symbol, preferably a number, which is clearly visible to those with normal color vision, and invisible, or difficult to see, to those with a red-green (or other) color vision defect.

Still referring to FIG. 3, once the patient perceives the test symbol the test data is captured 414 the opacity (or index)

of the cataract is calculated as described earlier. The test data may be stored for later retrieval and analysis in a local medical record 43 or in a network or cloud storage 44.

It should be understood that the foregoing description is only illustrative of the invention. Thus, various alternatives and modifications can be devised by those skilled in the art without departing from the invention. Accordingly, the present invention is intended to embrace all such alternatives, modifications and variances that fall within the scope of the appended claims.

What is claimed is:

1. A method for noninvasive diagnosis and quantitative assessment of cataract development, the method comprising:
    superimposing a symbol field (SF) over a background field (BF), wherein SF and BF comprise a plurality of pixelated dots having Red, Green, Blue (RGB) values;
    determining the RGB values for SF to be discernable from BF with a cataract free lens;
    recording RGB values for the cataract free lens;
    viewing the SF and the BF simultaneously with a cataract lens;
    adjusting the RGB values until SF is discernable from BF;
    recording RGB values for the cataract lens; and
    determining the opacity of the cataract lens from the recorded RGB values.

2. The method as, in claim 1, wherein determining the RGB values for SF to be discernable from BF with a cataract free lens comprises adjusting in-situ the RGB values with a user's cataract fee lens.

3. The method as in claim 1, wherein determining the RGB values for SF to be discernable from BF with a cataract free lens comprises retrieving RGB values from memory storage.

4. The method as in claim 1 further comprising:
    determining a B1 value, wherein determining the B1 value comprises:
        setting a background field (BF) Red, Green, Blue (RGB) values to BF predetermined values;
        setting a symbol, field (SF) Red, Green, Blue (RGB) values to BF predetermined values;
        observing SF superimposed on BF simultaneously via a cataract free lens;
        increasing SF B until SF is observable via the cataract free lens;
        recording SF B as the B1 value;
    determining a B2 value, wherein determining the B2 value comprises:
        setting the background field (BF) Red, Green, Blue (RGB) values to the BF predetermined values;
        setting the symbol field (SF) Red, Green, Blue (RGB) values, to the BF predetermined values;
        observing SF superimposed on BF simultaneously via a cataract lens;
        increasing SF B until SF is observable via the cataract, lens;
        recording SF Bas the B2 value;
    calculating the opacity of the cataract lens $OC_s$ as the absolute difference between B1 and B2; and
    saving $OC_s$.

5. The method as in claim 1 further comprising:
    determining a B1 value, wherein determining the B1 value comprises:
        setting a background field (BF) Red, Green, Blue (RGB) values to BF predetermined values;
        setting a symbol field (SF) Red, Green, Blue (RGB) values to BF predetermined values;
        observing SF superimposed on BF simultaneously via a cataract free lens;
        increasing BF B until SF is observable via the cataract free lens;
        recording BF B as the B1 value;
    determining a B2 value, wherein determining the B2 value comprises:
        setting the background field (BF) Red, Green, Blue (RGB) values to the BF predetermined values;
        setting the symbol field (S F) Red, Green, Blue (RGB) values to the BF predetermined values;
        observing SF superimposed on BF simultaneously via a cataract lens;
        increasing BF B until SF is observable via the cataract lens;
        recording BF B as the B2 value;
    calculating the opacity of the cataract lens $OC_b$ as the absolute difference between B1 and B2; and
    saving $OC_b$.

6. A mobile apparatus comprising a set of executable instructions that configures the mobile apparatus to determine an opacity of a cataract lens, the executable instructions comprising:
    superimposing a symbol field (SF) over a background field (BF), wherein SF and BF comprise a plurality of pixelated dots having Red, Green, Blue (RGB) values;
    determining the cataract free RGB values for SF to be discernable from BF;
    recording the cataract free RGB values;
    viewing the SF and the BF simultaneously with a cataract lens;
    adjusting the cataract lens RGB values until SF is discernable from BF;
    recording cataract lens RGB values for the cataract lens; and
    determining the opacity of the cataract lens from the recorded RGB values.

7. The mobile apparatus of claim 6, wherein determining the cataract free RGB values for SF to be discernable from BF comprises adjusting in-situ the RGB values with a user's cataract free lens.

8. The mobile apparatus of in claim 6, wherein determining the cataract free RGB values for SF to be discernable from BF comprises retrieving RGB values from memory storage.

9. The mobile apparatus of in claim 6 further comprising:
    determining a B1 value, wherein determining the B1 value comprises:
        setting the background field (BF) Red, Green, Blue (RGB) values to BF predetermined values;
        setting the symbol field (SF) Red, Green, Blue (RGB) values to BF predetermined values;
        observing SF superimposed on BF simultaneously via a cataract free lens;
        increasing SF B until SF is observable via the cataract free lens;
        recording SF B as the B1 value;
    determining a B2 value, wherein determining the B2 value comprises:
        setting the background field (BF) Red, Green, Blue (RGB) values to the BF predetermined values;
        setting the symbol field (SF) Red, Green, Blue (RGB) values to the BF predetermined values;
        observing SF superimposed on BF simultaneously via a cataract lens;
        increasing SF B until Sf is observable via the cataract lens;

calculating the opacity of the cataract lens OCs as the absolute difference between B1 and B2; and
saving OCs.

10. The mobile apparatus of claim 6 further comprising:
determining a B1 value, wherein determining the B1 value comprises:
  setting the background field (BF) Red, Green, Blue (RGB) values to the BF predetermined values;
  setting the symbol field (SF) Red, Green, Blue (RGB) values to the BF predetermined values;
  observing SF superimposed on BF simultaneously via a cataract free lens;
  increasing BF B until SF is observable via the cataract free lens;
  recording BF B as the B1 value;
determining a B2 value, wherein determining the B2 value comprises:
  setting the background field (BF) Red, Green, Blue (RGB) values to the BF predetermined values;
  setting the symbol field (SF) Red, Green, Blue (RGB) values to the BF predetermined values;
  observing SF superimposed on BF simultaneously via a cataract lens;
  increasing BF B until SF is observable via the cataract lens;
  recording BF B as the B2 value;
  calculating the opacity of the cataract lens OCb as the absolute difference between B1 and B2; and
  saving OCb.

11. The mobile apparatus of claim 6 further comprising:
setting a second background field (SBF) Red, Green, Blue (RGB) values to second BF predetermined values;
setting a second symbol field (SSF) Red, Green, Blue (RGB) values to SSF predetermined values;
observing SSF superimposed on SBF simultaneously; and
determining colorblindness.

\* \* \* \* \*